United States Patent
Alessi et al.

(10) Patent No.: US 9,856,522 B2
(45) Date of Patent: Jan. 2, 2018

(54) METHOD, MICROREACTOR AND APPARATUS FOR CARRYING OUT REAL-TIME NUCLEIC ACID AMPLIFICATION

(75) Inventors: Enrico Alessi, Catania (IT); Daniele Ricceri, Catania (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 1174 days.

(21) Appl. No.: 13/142,852

(22) PCT Filed: Dec. 15, 2009

(86) PCT No.: PCT/EP2009/067167
§ 371 (c)(1),
(2), (4) Date: Dec. 12, 2011

(87) PCT Pub. No.: WO2010/076189
PCT Pub. Date: Jul. 8, 2010

(65) Prior Publication Data
US 2012/0108454 A1 May 3, 2012

(30) Foreign Application Priority Data
Dec. 30, 2008 (IT) .............................. TO2008A1016

(51) Int. Cl.
*C12Q 1/68* (2006.01)
(52) U.S. Cl.
CPC ........... *C12Q 1/6837* (2013.01); *C12Q 1/686* (2013.01); *C12Q 1/6844* (2013.01)
(58) Field of Classification Search
None
See application file for complete search history.

(56) References Cited

U.S. PATENT DOCUMENTS

| | | | | |
|---|---|---|---|---|
| 2006/0177841 A1* | 8/2006 | Wangh et al. | | 435/6 |
| 2009/0191618 A1 | 7/2009 | Remacle et al. | | |
| 2009/0269737 A1* | 10/2009 | Ollikka | | 435/6 |

FOREIGN PATENT DOCUMENTS

| | | |
|---|---|---|
| EP | 1788097 | 5/2007 |
| EP | 1788097 A1 * | 5/2007 |
| EP | 1 942 196 A2 | 7/2008 |
| WO | 03/034029 A2 | 4/2003 |
| WO | WO2006135437 | 12/2006 |
| WO | WO 2006135437 A2 * | 12/2006 |
| WO | WO2008014485 | 1/2008 |
| WO | WO 2008014485 A2 * | 1/2008 |

OTHER PUBLICATIONS

Hubert Zipper, Investigations on DNA intercalation and surface binding by SYBR Green I, its structure determination and methodological implications, Nucleic Acids Research, vol. 32 No. 12 e103, Oxford University Press 2004.

* cited by examiner

*Primary Examiner* — Prabha Chunduru
(74) *Attorney, Agent, or Firm* — Seed IP Law Group LLP

(57) ABSTRACT

A method for carrying out nucleic acid amplification, includes providing a reaction chamber (31), accommodating an array (36) of nucleic acid probes (37) at respective locations; for hybridizing to respective target nucleic acids; and introducing a solution (50) into the reaction chamber (31), wherein the solution (50) contains primers, capable of binding to target nucleic acids, nucleotides, nucleic acid extending enzymes and a sample including nucleic acids. The structure of the nucleic acid probes (37) and of the primers is selected so that a hybridization temperature ($T_H$) of the probes (37) is higher than an annealing temperature ($T_A$) of the primers, whereby hybridization and annealing take place in respective separate (non-overlapping) temperature ranges ($R_H$, $R_A$).

7 Claims, 2 Drawing Sheets

METHOD, MICROREACTOR AND APPARATUS FOR CARRYING OUT REAL-TIME NUCLEIC ACID AMPLIFICATION

PRIOR RELATED APPLICATIONS

This application is a 35 U.S.C. Section 371 of PCT/EP2009/067167, filed Dec. 15, 2009, which claims priority to Italian Serial No. TO2008A 001016, filed Dec. 30, 2008, and both are incorporated in their entireties by reference herein.

TECHNICAL FIELD

The present invention relates to a method, to a microreactor and to an apparatus for carrying out real-time nucleic acid amplification. In particular, amplification process exploits an array of oligonucleotide probes.

BACKGROUND ART

Typical procedures for analyzing biological materials, such as nucleic acid, protein, lipid, carbohydrate, and other biological molecules, involve a variety of operations starting from raw material. These operations may include various degrees of cell separation or purification, cell lysis, amplification or purification, and analysis of the resulting amplification or purification product.

As an example, in DNA-based blood analyses samples are often purified by filtration, centrifugation or by electrophoresis so as to eliminate all the non-nucleated cells, which are generally not useful for DNA analysis. Then, the remaining white blood cells are broken up or lysed using chemical, thermal or biochemical means in order to liberate the DNA to be analyzed. Next, the DNA is denatured by thermal, biochemical or chemical processes and amplified by an amplification reaction, such as PCR (polymerase chain reaction), LCR (ligase chain reaction), SDA (strand displacement amplification), TMA (transcription-mediated amplification), RCA (rolling circle amplification), and the like. The amplification step allows the operator to avoid purification of the DNA being studied because the amplified product greatly exceeds the starting DNA in the sample.

If RNA is to be analyzed the procedures are similar, but more emphasis is placed on purification or other means to protect the labile RNA molecule. RNA is usually copied into DNA (cDNA) and then the analysis proceeds as described for DNA.

Finally, the amplification product undergoes some type of analysis, usually based on sequence or size or some combination thereof. In an analysis by microarray hybridization, for example, the amplified DNA is passed over a plurality of detectors made up of individual oligonucleotide detector fragments that are anchored, for example, on electrodes. If the amplified DNA strands are complementary to the oligonucleotide detectors or probes, stable bonds will be formed between them (hybridization) under specific temperature conditions. The hybridized detectors can be read by observation using a wide variety of means, including optical, electromagnetic, electromechanical or thermal means.

Other biological molecules are analyzed in a similar way, but typically molecule purification is substituted for amplification, and detection methods vary according to the molecule being detected. For example, a common diagnostic involves the detection of a specific protein by binding to its antibody. Such analysis requires various degrees of cell separation, lysis, purification and product analysis by antibody binding, which itself can be detected in a number of ways. Lipids, carbohydrates, drugs and small molecules from biological fluids are processed in similar ways. However, we have simplified the discussion herein by focusing on nucleic acid analysis, in particular DNA analysis, as an example of a biological molecule that can be analyzed using the devices of the invention.

PCR is time consuming, because it is necessary to perform 20-30 iterations of the basic thermal cycle to ensure that any target nucleic acid has been sufficiently amplified so as to be detectable. Further, the amplification and detection reactions are often sequential, further consuming valuable time.

DISCLOSURE OF INVENTION

The object of the invention is to provide a method, a microreactor and an apparatus for carrying out real time nucleic acid amplification that is free from the above described limitations.

According to the present invention, a method, a microreactor and an apparatus for carrying out nucleic acid amplification are provided, as claimed in claims 1, 9 and 10, respectively.

BRIEF DESCRIPTION OF THE DRAWINGS

For the understanding of the present invention, some embodiments thereof will be now described, purely as non-limitative examples, with reference to the enclosed drawings, wherein.

BEST MODE FOR CARRYING OUT THE INVENTION

Figure 1:
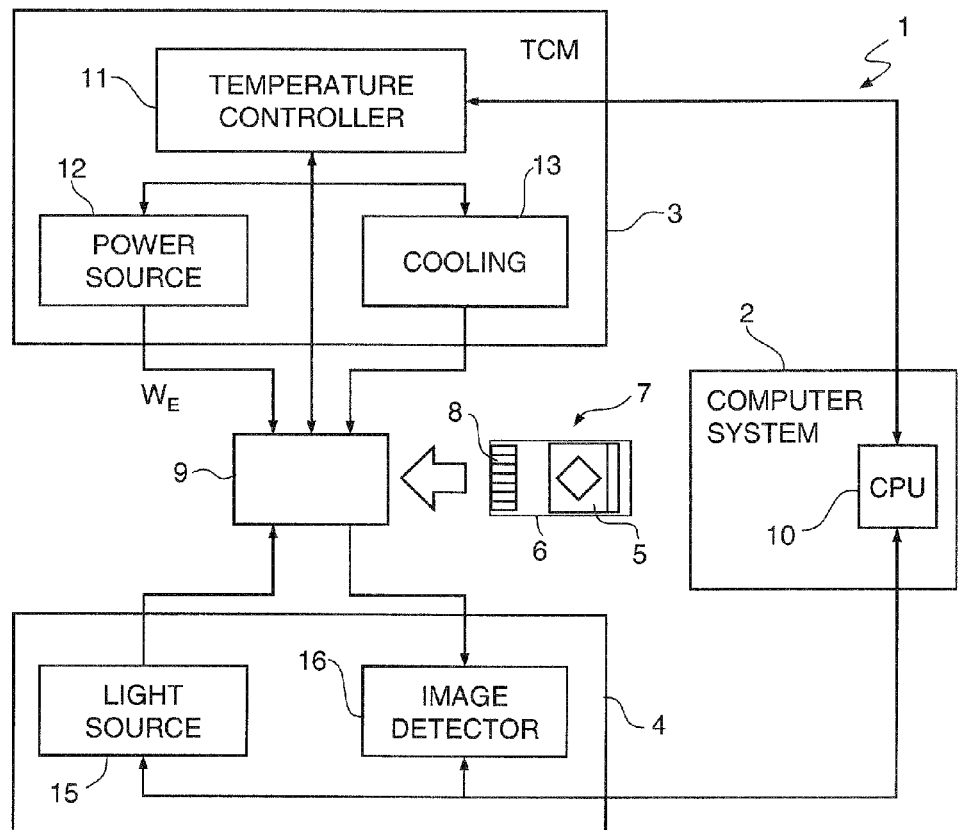
FIG. 1 is a system depiction of an apparatus for carrying out nucleic acid amplification according to one embodiment of the present invention.

With reference to FIG. 1, a biochemical analysis apparatus 1 comprises a computer system 2, a temperature control module 3, a reader device 4, and a microreactor 5 for performing biochemical analyses, that is provided on a board 6 to form a disposable microreactor cartridge 7.

The microreactor cartridge 7 is loadable into a receptacle 9 of the apparatus 1 and is provided with an interface 8 for coupling with the temperature control module 3 and the reader device 4.

The temperature control module 3 and the reader device are both controlled by a processing unit 10 of the computer system 2.

The temperature control module 3 includes a temperature controller 11 and a power source 12. The temperature controller 11 is configured to receive a temperature signal $S_T$ from a temperature sensor (described later on and here not shown) on the microreactor cartridge 7. The temperature control module 3 may also include a cooling element 13, e.g. a Peltier module or a fan coil, which is controlled by the temperature controller 11 and is thermally coupled to the microreactor 5 when the cartridge 7 is loaded in the reader device 4. The power source 12 and the cooling element 13 are operable by the temperature controller 11 respectively to deliver power to heaters (also described later on and here not shown) coupled to the microreactor 5 and to cool the cartridge 7, in order to set an operating temperature in accordance with a temperature profile (see e.g., FIG. 5).

In one embodiment, the reader device 4 is configured to perform optical detection of the reaction products in the microreactor 5, as hereinafter described. In particular, the reader device 4 includes a light source 15 for illuminating the microreactor 5 with light at an excitation wavelength; and an image detector 16, configured to receive fluorescence radiation emitted from the microreactor 5, in response to the light at the excitation wavelength. However, it is understood that other ways to carry out detection are available and can be exploited, in place of optical detection. For example electrochemical detection can be performed.

Figure 2:
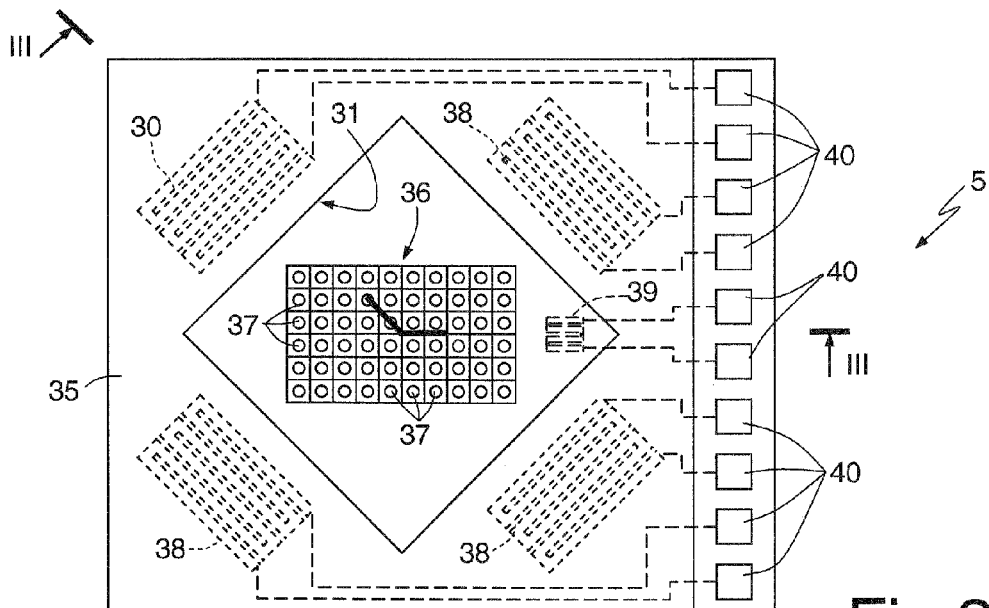
FIG. 2 is a top plan view of a microreactor according to one embodiment of the present invention.
Figure 3:
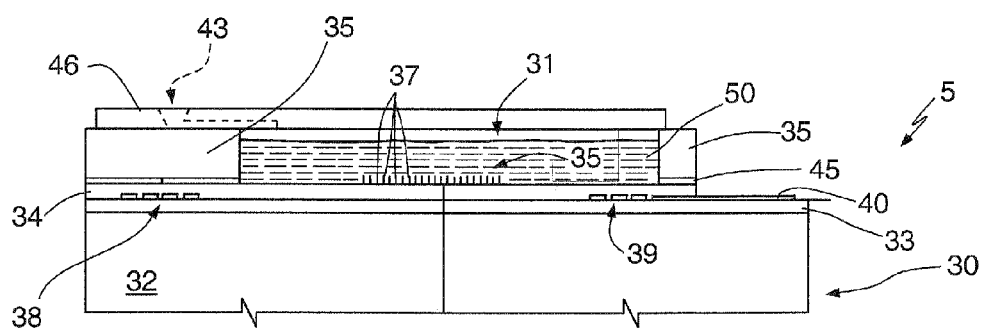
FIG. 3 is a cross-sectional view of the microreactor of FIG. 2, taken along the line III-III of FIG. 2.

FIGS. 2 and 3 illustrate in detail one embodiment of the microreactor 5. However, it is understood that the configuration of the microreactor 1 herein illustrated and described can not be considered in any way limiting and numerous different configurations could be exploited as well.

The microreactor 5 comprises a body 30, having a recess wherein a reaction chamber 31 is formed.

The body 30 includes a substrate 32, covered with a stack of layers including, in one embodiment, a dielectric layer 33, a passivation layer 34 and a structural layer 35. The reaction chamber 31 is formed in the structural layer 35 and is downwardly delimited by the passivation layer 34.

A microarray 36 of DNA probes 37 is accommodated in the reaction chamber 31, while heaters 38 and a temperature sensor 39 are embedded in the passivation layer 34. Probes include a variety of short oligonucleotide sequences that are placed at specific locations of the microarray 36.

The substrate 32 is made of a thermally conductive material, such as undoped silicon.

In one embodiment, the dielectric layer 33 is of silicon dioxide and has a thickness of e.g. 0.1 μm to 1 μm. The heaters 38 and the temperature sensor 39 are arranged on the dielectric layer 33 and therefore they are electrically insulated from the substrate 32. However, due to the small thickness of the dielectric layer 33, the heaters 38 and the temperature sensor 39 are thermally coupled to the substrate 32. Moreover, the heaters 38 and the temperature sensor 39 are electrically connected to respective pads 40, for coupling with the temperature control module 3 and reader device 4 through the interface 8 of the cartridge 7. When the cartridge 7 is loaded into the receptacle 9 (FIG. 1), the heaters 38 are connected to the power source 12 for receiving electrical power and the temperature sensor 39 is connected to the temperature controller unit 11 for providing a temperature signal $S_T$.

The passivation layer 34, also of silicon dioxide, is arranged between the dielectric layer 13 and the structural layer 35 and incorporates the heaters 38 and the temperature sensor 39. A top surface of the passivation layer 34 defines a bottom wall of the reaction chamber 31.

The structural layer 35, e.g. of silicon or glass, is bonded to the passivation layer 34 and has an opening therein defining the reaction chamber 31. The design of the heaters 38 may be optimized according to individual configurations of the reaction chamber 31, in order to achieve desired temperature profiles. The temperature sensor 39 is preferably arranged under the reaction chamber 31.

The reaction chamber 31 is closed by a transparent cap layer 46 (not shown in FIG. 2), attached or bonded to the structural layer 35, and which may have a small opening 43 for introducing samples to the reaction chamber 31.

The microarray 36 comprises a plurality of nucleic acid probes 37, preferably single strand deoxy-oligonucleotides, grafted to the passivation layer 34 at respective locations. Probes 37 are designed to hybridize to target DNA at a specific hybridization temperature when a reaction, such as nucleic acid amplification, is carried out in the reaction chamber 31.

Figure 4:
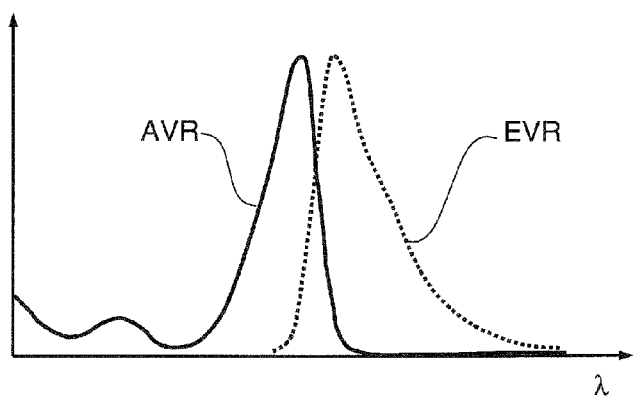
FIG. 4 is a plot showing absorption and emission spectra of a dye-DNA complex.

Hereinafter reference will be made to a nucleic acid analysis process including PCR (Polymerase Chain Reaction). As is known, PCR is a cyclical process involving a series of enzyme-mediated reactions whose final result are identical copies of the target nucleic acid. A raw biological sample is preliminarily processed by conventional steps of cell separation or purification and cell lysis. Then, the sample is added to a solution comprising enzymes (typically a DNA polymerase such as TAQ), primers, the four nucleotides (collectively referred to as dNTPs), cofactor, buffer, and a fluorescent dye capable of binding to double-helix DNA. Such dyes include, but are not limited, bisbenzimide or indole-derived stains (Hoechst 33342, Hoechst 33258 and 4',6-diamidino-2-phenylindole), phenanthridinium stains (ethidium bromide and propidium iodide) and cyanine dyes (PicoGreen, YOYO-1 iodide, SYBR Green I and SYBR Gold). The fluorescent dye is preferably selected from the group of cyanine dyes and, in one example, is SYBR Green I. As illustrated in FIG. 4, a dye-DNA complex, that forms during the amplification process, adsorbs visible radiation AVR selectively around a wavelength of 488 nm (blue) and emits visible radiation EVR with a maximum of emission at 522 nm (green).

The sequences of the probes 37 and of the primers determine a hybridization temperature, at which the probes 37 hybridize to complementary target DNA single strands, and an annealing temperature, at which the primers bind to their complementary sequences on the target DNA. In one embodiment, the probes 37 and the primers are selected such that the hybridization temperature is higher than the annealing temperature, so that hybridization and annealing take place in separate and spaced apart (non overlapping) temperature ranges. Thus, at the hybridization temperature, primer annealing is prevented and at the annealing temperature the primers are allowed to bind to denatured target DNA.

Apart from parameters of the solution (such as salinity), the hybridization and annealing temperatures are determined by the sequence of the probes 37 and of the primers. Namely, for complementary DNA strands, the highest hybridization rate is achieved at a temperature of about 20-25° C. below the melting temperature of the DNA helix. For probes 37, that are composed of short nucleotide sequences, the hybridization temperature is about 5-10° C. below the melting temperature.

Thus, once the composition of the solution has been defined, the hybridization temperature may be determined by setting the melting temperature of the probe-target DNA pair. The melting temperature of a hybrid in a solution, such as a probe-target DNA pair, is given by $$T_M = 81.5 + 16.6(\log M) + 0.41(\% \ G+C) - 0.61(\% \ \text{form}) - 500/L$$

where $T_M$ is the melting temperature, M is the molarity of univalent cations, (% G+C) is the percentage of guanine and cytosine, (% form) is the percentage of formamide and L is the coupling length, i.e. the length of the sequence in terms of number of paired bases.

If coupling length L is less than 50, however, the melting temperature is preferably determined from the equation:

$$T_M = 2N_{AT} + 4N_{GC}$$

where $N_{AT}$ is the number of A-T (adenine-thymine) pairs and $N_{GC}$ is the number of G-C (guanine-cytosine) pairs in the sequence.

In both cases, however, the melting temperature $T_M$ in a given solution is essentially determined by the number of G-C pairs and by the coupling length L. Thus, the sequence of the probes 37 and of the primers, namely the number of G-C pairs and the coupling length L, can be selected to set the hybridization temperature and the annealing temperature such that annealing is prevented during hybridization and vice versa.

By way of example, a primer may be defined by a sequence of 19 dNTPs (to have a corresponding coupling length of 19), capable of forming 9 A-T pairs and 10 G-C pairs upon annealing. Once a salinity of the solution has been defined, the primer melting temperature $T_{MPRIMER}$ can be calculated. If the primer melting temperature $T_{MPRIMER}$ is determined to be e.g. 57° C., the annealing temperature is about 52° C. (approximately 5° C. less than the primer melting temperature $T_{MPRIMER}$). A probe 37 having 50 bases may be selected from a sequence with high content of guanine and cytosine, to have high probe melting temperature $T_{MPROBE}$ and hybridization temperature. In one example, the probe 37 may be defined by a sequence of 50 dNTPs (to have a corresponding coupling length of 50) and contains 54% of guanine-cytosine and 46% of adenine-thymine. In the same solution, the probe melting temperature $T_{MPROBE}$ of the described probe 37 would be 85° C. and the hybridization temperature about 80° C. (again, 5° C. less than the probe melting temperature $T_{MPROBE}$.) Thus, hybridization and annealing take place at separate temperature intervals and are selectively and exclusively carried out. In other words, when the primers can bind to target DNA, the probes 37 cannot hybridize and, vice versa, when the temperature conditions allow hybridization, annealing is prevented.

At the annealing temperature, the probes 37 are not active and do not interact with target DNA. Hence, the hybridization of the probes 37 can be avoided, although the DNA amplification process is carried out in the same reaction chamber 31 accommodating the microarray 36.

To start an analysis process involving PCR, a solution 50, obtained as described above, is supplied to the reaction chamber 31 and the microreactor 5 is loaded into the receptacle 9 of the apparatus 1.

DNA amplification by PCR is then carried out in the reaction chamber 31. To this end, the temperature controller 11 operates the power source 12 and the cooling element 13 to controllably deliver electric power $W_E$ to the heaters 38 and to cyclically control an operating temperature $T_O$ of the solution 50 in the reaction chamber 31 in accordance with a desired amplification temperature profile.

Figure 5:
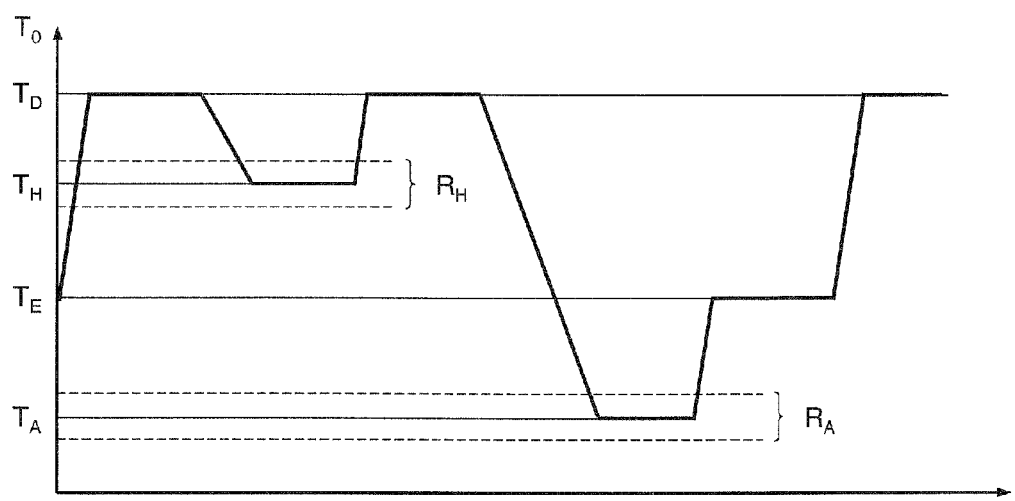
FIG. 5 is a temperature profile used in a method according to one embodiment of the present invention.

An example of an amplification temperature profile for the operating temperature $T_O$ during a PCR amplification cycle is shown in FIG. 5. PCR amplification cycles are iteratively carried out until stop conditions are met. A hybridization range $R_H$ and an annealing range $R_A$, separate and non overlapping, are also illustrated in FIG. 5.

Double stranded DNA is first denatured at a denaturation temperature $T_D$ (94° C. for 10 s to 60 s). In this step, DNA helixes separate into single strands.

Then, the solution is set at about a hybridization temperature $T_H$ of the hybridization range $R_H$, at which the hybridization rate of the probes 37 is maximum. Selective hybridization of the probes 37 to any complementary target DNA is thus carried out. The hybridization temperature $T_H$ of the probes 37 is determined as above explained and is lower than the denaturation temperature $T_D$. With reference to the probe sequence and solution composition already referred to, the hybridization temperature $T_H$ is about 80° C. At the hybridization temperature $T_H$, the probes 37 of the microarray 36 are available for binding to complementary DNA strands provided in the solution 50. Annealing of the primers, however, does not take place at this temperature.

Optical detection of hybridized probes 37 is carried out as long as the hybridization temperature $T_H$ is maintained in the reaction chamber 31. Fluorescent dyes contained in the solution 30 bind to hybridized probes 37. Thus, hybridized probes 37 respond to a confocal light stimulation from a source at a source wavelength (488 nm in the example described) and emit visible radiation at an emission wavelength (522 nm), greater than the source wavelength.

After first denaturation, hybridization and detection, double stranded DNA is again denatured at the denaturation temperature $T_D$. The first and second denaturation may have the same duration, in one embodiment. Fluorescent molecules are then released in the solution after the second denaturation, due to separation of target DNA from the respective probes 37.

Then, the solution 50 in the reaction chamber 31 is cooled to about an annealing temperature $T_A$ in the annealing range $R_A$, that in one embodiment may be of 50° C. to 70° C. (for 10 s to 60 s). In one embodiment, in particular, the annealing temperature $T_A$ is 68°. At this stage, primers, which are more numerous than the probes, effectively compete for and bind to their complementary sequences in the floating target DNA thus allowing amplification of target sequences.

Finally, the solution is heated to an extension temperature $T_E$, at which DNA polymerase extends primers, by adding nucleotides that are complementary to the target strand. The extension temperature $T_E$ is intermediate between the annealing temperature $T_A$ and the hybridization temperature $T_H$ (e.g. 72° C., for 10 s to 60 s). During extension, the fluorescent molecules can bind the PCR product, so that a new optical detection of floating DNA may be carried out. However, in this case information related to probe location and type would be lost, so different species of amplified target DNA cannot be distinguished at this stage of the cycle. However, the signal will be diffused throughout the entire solution, and be less intense that the localized signal that occurs when the localized probes hybridize to target.

During each cycle, the heating rate is preferably at least 5-7° C./s, while the cooling rate is preferably greater than 10° C./s.

The hybridization and annealing/amplification cycles may be repeated until sufficient copies of the target DNA have been produced as to be detectable. The amplification process may then be interrupted upon positive detection of the searched target DNA, or after a threshold number of cycles, if the target DNA is not detected (it is thus determined that the starting sample did not contain the target DNA).

Thus, real-time detection of multiple target DNA is possible, because hybridization of the probes and primer annealing take place at separate temperatures. In turn, real-time detection allows the operator to reduce the average duration of amplification processes, because amplification may be interrupted as soon as the amount of target DNA becomes detectable. Moreover, use of a microarray of probes allows the operator to simultaneously detect the presence or absence of numerous different target DNA through a single fluorescent dye. In fact, different probes are usually provided at different locations in the microarray, thus the location at which hybridization of a probe is detected carries also information on the nature of the target DNA bound to the probe.

Finally, it is clear that numerous modifications and variations may be made to the method and apparatus described and illustrated herein, all falling within the scope of the invention, as defined in the attached claims.

The invention claimed is:

1. A microreactor comprising:
    a reaction chamber including an array of nucleic acid probes at respective locations, the nucleic acid probes being configured to hybridize to respective target nucleic acids at a hybridization temperature range ($R_H$); and
    a solution in the reaction chamber, wherein the solution contains primers configured to bind to target nucleic acids, nucleotides, nucleic acid extending enzymes and nucleic acids at an annealing temperature range ($R_A$);
    wherein both said nucleic acid probes and said primers are structured so that said hybridization temperature range is higher than and does not overlap with said annealing temperature range.

2. A microreactor according to claim 1, further comprising a temperature control module for cyclically controlling an operative temperature ($T_O$) of the solution in accordance with a temperature profile.

3. A microreactor according to claim 2, wherein the temperature control module is configured to set the solution to a first temperature ($T_H$) within the hybridization temperature range ($R_H$), in which hybridization of the probes is allowed, and to set the solution to a second temperature ($T_A$) within the annealing temperature range ($R_H$), in which annealing of the primers is allowed.

4. A microreactor according to claim 2, wherein the temperature control module comprises a temperature controller, a power source and a cooling element, both controlled by the temperature controller and operable to respectively heat and cool the microreactor in accordance with the temperature profile.

5. A microreactor according to claim 3, further comprising a reader device and wherein the microreactor is mounted on a board to form a cartridge loadable into the reader device.

6. A microreactor according to claim 5, wherein the reader device is an optical reader.

7. A microreactor according to claim 6, wherein the reader device includes:
    a light source for illuminating the microreactor with light at an excitation wavelength, when the cartridge is loaded in the reader device; and
    an image detector, configured to receive fluorescence radiation emitted the microreactor, in response to the light at the excitation wavelength.

* * * * *

UNITED STATES PATENT AND TRADEMARK OFFICE
CERTIFICATE OF CORRECTION

PATENT NO. : 9,856,522 B2
APPLICATION NO. : 13/142852
DATED : January 2, 2018
INVENTOR(S) : Enrico Alessi et al.

It is certified that error appears in the above-identified patent and that said Letters Patent is hereby corrected as shown below:

On the Title Page

Item (57) Abstract:
"A method for carrying out nucleic acid amplification, includes providing a reaction chamber (31), accommodating an array (36) of nucleic acid probes (37) at respective locations; for hybridizing to respective target nucleic acids; and introducing a solution (50) into the reaction chamber (31), wherein the solution (50) contains primers, capable of binding to target nucleic acids, nucleotides, nucleic acid extending enzymes and a sample including nucleic acids. The structure of the nucleic acid probes (37) and of the primers is selected so that a hybridization temperature ($T_H$) of the probes (37) is higher than an annealing temperature ($T_A$) of the primers, whereby hybridization and annealing take place in respective separate (non-overlapping) temperature ranges ($R_H$, $R_A$)." should read, -- A method for carrying out nucleic acid amplification, includes providing a reaction chamber (31), accommodating an array (36) of nucleic acid probes (37) at respective locations, for hybridizing to respective target nucleic acids; and introducing a solution (50) into the reaction chamber (31), wherein the solution (50) contains primers, capable of binding to target nucleic acids, nucleotides, nucleic acid extending enzymes and a sample including nucleic acids. The structure of the nucleic acid probes (37) and of the primers is selected so that a hybridization temperature ($T_H$) of the probes (37) is higher than an annealing temperature ($T_A$) of the primers, whereby hybridization and annealing take place in respective separate (non-overlapping) temperature ranges ($R_H$, $R_A$). --.

In the Claims

Column 8, Line 25:
"radiation emitted the microreactor, in response to the" should read, -- radiation emitted from the microreactor, in response to the --.

Signed and Sealed this
Eighteenth Day of June, 2019

Andrei Iancu
*Director of the United States Patent and Trademark Office*